United States Patent
Liang et al.

(10) Patent No.: US 9,279,120 B2
(45) Date of Patent: Mar. 8, 2016

(54) IMPLANTABLE DEVICES HAVING CERAMIC COATING APPLIED VIA AN ATOMIC LAYER DEPOSITION METHOD

(75) Inventors: Xinhua Liang, Boulder, CO (US); Alan W. Weimer, Niwot, CO (US); Stephanie J. Bryant, Boulder, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 357 days.

(21) Appl. No.: 12/464,925

(22) Filed: May 13, 2009

(65) Prior Publication Data

US 2009/0304774 A1    Dec. 10, 2009

Related U.S. Application Data

(60) Provisional application No. 61/127,529, filed on May 14, 2008.

(51) Int. Cl.
| | | |
|---|---|---|
| *C12N 11/14* | (2006.01) | |
| *A61L 27/14* | (2006.01) | |
| *A61L 27/30* | (2006.01) | |
| *A61L 27/56* | (2006.01) | |
| *C12N 5/00* | (2006.01) | |

(52) U.S. Cl.
CPC ............... *C12N 11/14* (2013.01); *A61L 27/14* (2013.01); *A61L 27/306* (2013.01); *A61L 27/56* (2013.01); *C12N 5/0068* (2013.01); *C12N 2533/14* (2013.01); *Y10T 428/249967* (2015.04)

(58) Field of Classification Search
None
See application file for complete search history.

(56) References Cited

U.S. PATENT DOCUMENTS

| | | | |
|---|---|---|---|
| 7,338,517 B2 | 3/2008 | Yost | |
| 7,955,704 B2 * | 6/2011 | Lowery et al. | 428/451 |
| 2006/0134433 A1 * | 6/2006 | Maula et al. | 428/411.1 |
| 2006/0204738 A1 * | 9/2006 | Dubrow et al. | 428/292.1 |
| 2007/0125702 A1 * | 6/2007 | Ramaswamy et al. | 210/490 |
| 2008/0015709 A1 * | 1/2008 | Evans et al. | 623/23.51 |
| 2009/0022775 A1 * | 1/2009 | Champ et al. | 424/423 |
| 2009/0137043 A1 * | 5/2009 | Parsons et al. | 435/398 |
| 2011/0054633 A1 * | 3/2011 | Miller et al. | 623/23.72 |

FOREIGN PATENT DOCUMENTS

WO    2007/124511 A    11/2007

OTHER PUBLICATIONS

Rezwan, K. Che, Q.Z., Blaker, J.J., Boccaccini, A.R. Biodegradable and bioactive porous polymer/inorganic composite scaffolds for bone tissue engineering. Biomaterials 27:3413-3431, 2006.*
Boccaccini et al., "Poly(D,L-lactide) (PDLLA) foams with TiO2 nanoparticles and . . ." J Materials Sci (2006) vol. 41, pp. 3999-4008.

* cited by examiner

*Primary Examiner* — Robert A Wax
*Assistant Examiner* — Danah Al-Awadi
(74) *Attorney, Agent, or Firm* — Gary C Cohn PLLC

(57) ABSTRACT

Substrates coated with films of a ceramic material such as aluminum oxides and titanium oxides are biocompatible, and can be used in a variety of applications in which they are implanted in a living body. The substrate is preferably a porous polymer, and may be biodegradable. An important application for the ceramic-coated substrates is as a tissue engineering scaffold for forming artificial tissue.

11 Claims, 3 Drawing Sheets

IMPLANTABLE DEVICES HAVING CERAMIC COATING APPLIED VIA AN ATOMIC LAYER DEPOSITION METHOD

CROSS-REFERENCE TO RELATED APPLICATION

This application claims benefit of U.S. Provisional Application No. 61/127,529, filed 14 May 2008.

STATEMENT OF GOVERNMENT INTEREST

This invention was made with government support under contract number DE-FG02-03ER86157 awarded by the U.S. Department of Energy and contract number CMM0400292 awarded by the National Science Foundation. The government has certain rights in the invention.

BACKGROUND OF THE INVENTION

This invention relates to implantable devices such as tissue engineering scaffolds.

Many complex animal tissues cannot regenerate after certain injury or disease. In other cases, animal tissues are damaged or malformed due to congenital or developmental defects. One approach to repairing tissue in these cases is known as tissue engineering. Tissue engineering is performed by providing a "scaffold" which serves as a matrix upon which cells can grow. Tissue structures are formed in vitro by growing cells on the scaffold. The structures can then be implanted into living organisms to repair natural tissues that have been damaged by disease or injury. Implantable devices of these types are of interest for repairing bone, ligaments, dental ligaments, tendons, epidermal tissue, muscle tissue (including cardiac tissue) and in other applications.

The scaffold material is usually a three-dimensional, porous structure. Porous polymers have attracted increased interest in the field of tissue engineering, because porous polymers have unique physicochemical properties, which can provide three dimensional structures as scaffolds to guide cell growth and tissue development. The ability of a cell to migrate and attach to a substrate or scaffold surface is an important attribute of the scaffold material. In addition, the scaffold material must be biocompatible and nontoxic.

Certain polymers are known to be highly biocompatible. Examples of these polymers include poly-L-lactic acid (or poly-L-lactide), copolymers of L-lactic acid or L-lactide with other alpha-hydroxyacids such as glycolic acid; copolymers of L-lactic acid or L-lactide with ethylene glycol; polyesters such as poly($\epsilon$-caprolactone), poly(3-hydroxybutyrate), poly (s-caproic acid), poly(p-dioxanone) and certain poly(ortho esters) such as polyol/diketene acetals addition polymers. These have been suggested for use as scaffold materials in, for example, U. S. Published Patent Application 2006/0263335 and 2007/0276509. Collagenous materials often are biocompatible and have been suggested for use as scaffold materials, for example, in U.S. Pat. No. 7,338,517.

The porous structure of pure polymers adversely impacts their mechanical properties and biocompatibility. Ceramics such as aluminum oxide and titanium oxide have excellent biocompatibility and bonds well to bone. See, e.g., K. Rezwan et al., "Biodegradable and bioactive porous polymer/inorganic composite scaffolds for bone tissue engineering", *Biomaterials*, 27 (2006) 3413; H. Warashina et al., "Biological reaction to alumina, zirconia, titanium and polyethylene particles implanted onto murine calvaria", *Biomaterials*, 24 (2003) 3655; and Y. Takami et al., "Biocompatibility of alumina ceramic and polyethylene as materials for pivot bearings of a centrifugal blood pump", *Journal of Biomedical Materials Research*, 36 (1997) 381. The inclusion of bioactive ceramic compositions in polymer substrates may reinforce the porous structures of the pure polymer and enhance the bioactivity and the tissue interaction. Therefore, hybrid three-dimensional porous scaffolds of synthetic or naturally derived biodegradable polymers and ceramics may be useful as bone replacement materials or as scaffolds for bone regeneration composition. These hybrid materials potentially exhibit favorable mechanical properties and bioactivity so that they can receive and respond to specific biological signals that direct and promote cell adhesion, proliferation and differentiation, and tissue regeneration.

In many practical applications, porous polymer/ceramic composites are often produced via incipient wetting methods such as casting, porogen leaching, and gas foaming. The solvent-based methods have the risk of leaving potentially toxic organic solvent residues. Dispersing micro-sized or nano-sized ceramic particles in the polymer matrix is another method that has been proposed to fabricate the polymer/ceramic composites. However, a potential negative effect of nanoparticle-containing scaffolds is the possibility of migration of nanoparticles within the body and their distribution via the blood stream, leading to pathologies of unknown origin. See, e.g., L. C. Gerhardt et al., "Titanium dioxide ($TiO_2$) nanoparticles filled poly(D,L lactic acid) (PDLLA) matrix composites for bone tissue engineering", *Journal of Materials Science-Materials in Medicine*, 18 (2007) 1287.

Therefore, there is a desire to produce a porous polymer/ceramic composite that is biocompatible, exhibits little toxicity towards cells (particularly mammalian cells and especially human cells) or the organism as a whole, and which has good mechanical properties. The composite should be a material to which cells and/or bone tissue can become easily attached. To accomplish this, the composite should have the ceramic material coated onto both the interior surfaces (i.e., the surfaces of the pores) as well as the exterior surfaces, and the pore size should be such that cells can migrate into the pores and become attached there.

SUMMARY OF THE INVENTION

This invention is in one aspect an implantable medical device, comprising a substrate material having a ceramic coating adherent to the surface of the substrate material, wherein the ceramic coating has a thickness of from about 1 to 100 nanometers and substantially covers the surfaces of the substrate material.

In certain embodiments, the invention is a porous tissue engineering scaffold comprising a porous polymer having a ceramic coating adherent to the surface of the porous polymer, wherein the ceramic coating has a thickness of from about 1 to 100 nanometers and substantially covers the external surface of the porous polymer and internal surfaces of the pores. The ceramic coating preferably is deposited on the porous polymer via an atomic layer deposition process. It may be an aluminum oxide or titanium oxide coating, and preferably is from 1 to 20 nanometers thick.

This invention is also an artificial tissue comprising living cells attached to the porous tissue engineering scaffold as described in the preceding paragraph. This invention is also a method for repairing or replacing tissue in a mammal, comprising applying this artificial tissue to a living mammal.

This invention is also a method for producing an artificial tissue, comprising (a) forming a tissue engineering scaffold by applying a ceramic coating to the external surface and the internal surfaces of the pores of a porous polymer via an atomic layer deposition process such that the ceramic coating has a thickness of from 1 to 100 nanometers and (b) growing cells in the presence of the tissue engineering scaffold such that living cells become attached to the tissue engineering scaffold. The invention is also a method for repairing or replacing tissue in a mammal, comprising applying an artificial tissue produced in this manner to a living mammal.

DETAILED DESCRIPTION OF THE INVENTION

Figure 1:
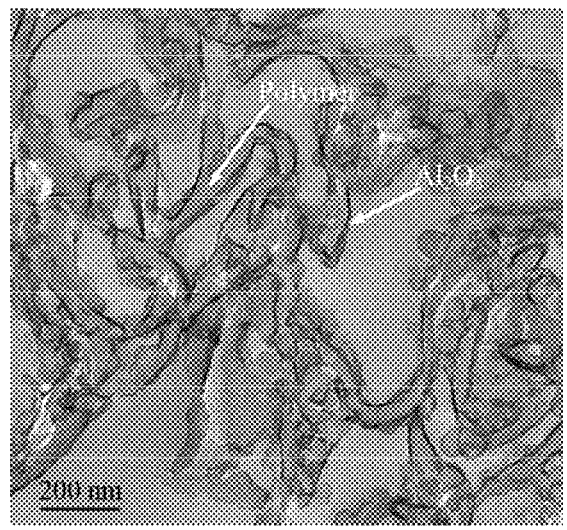
FIG. 1 is a TEM micrograph of a porous styrene-divinylbenzene copolymer having an atomic layer deposition aluminum oxide layer on the surface of the pores.

In this invention, various substrate materials that have an ultrathin layer of a ceramic material coated onto the exposed surfaces of the substrate are useful as all or a portion of various types of implanted devices. "Implanted devices" are devices that are implanted into or onto the body of a living animal and when implanted become in contact with living cells in the body of the animal. The coating of the ceramic material can provide several benefits, depending on the particular substrate material and the particular way in which the implanted device is used. For example, the ceramic coating can provide improved biocompatibility, can improve the ability of cells to adhere on and to the substrate, or can improve the ability of bone or other tissue to adhere to the implanted device.

In the broadest aspects of the invention, the substrate material can be any material that can be coated with the ceramic material. The substrate material itself may be a biocompatible material, but it does not have to be if the ceramic coating is capable of making the coated substrate sufficiently biocompatible to be used as an implant device.

A class of materials that are of particular interest as the substrate are organic polymers. These can be biopolymers, including collagen, fibronectin, laminin, elastin, fibrin, proteoglycans, hyaluronan and others as described, for example, in U.S. Pat. No. 7,338,517. The organic polymer may instead or in addition be a synthetic polymer. A synthetic polymer may be absorbable or nonabsorbable by the animal body in which it is implanted. Absorbable polymers include poly-L-lactic acid (or poly-L-lactide), copolymers of L-lactic acid or L-lactide with other alpha-hydroxyacids such as glycolic acid, copolymers of L-lactic acid or L-lactide with ethylene glycol; polyesters such as poly($\epsilon$-caprolactone), poly(3-hydroxybutyrate), poly(s-caproic acid), poly(p-dioxanone), or certain poly(ortho esters) such as polyol/diketene acetals addition polymers, as well as others as described in U. S. Published Patent Applications 2006/0263335 and 2007/0276509. Nonabsorbable polymers include a wide variety of thermoplastic or thermoset polymers, including polyethylene homopolymers and copolymers, styrene homopolymers and copolymers, crosslinked polystyrene, polyurethanes, polypropylene homopolymers or copolymers, polyamides, polyesters of various types, including polyalkyleneterephthalates, polyvinylidene fluoride, polycarbonates, polymers and copolymers of various acrylate and methacrylate esters, polyethers, including polyalkylene glycols such as polyethylene glycol, polytetrafluoroethylene and various blends and copolymers thereof. Dried hydrogels such as poly(2-hydroxyethyl methacrylate) and poly(ethylene glycol) can also serve as a porous polymeric substrate.

Porous substrate materials, especially porous organic polymer substrates, are of particular interest. For purposes of this invention, "pores" are voids in the structure of the substrate that communicate directly or indirectly with the surface of the polymer, i.e., which are open to the surface of the substrate. By contrast, void regions in the substrate that are not open to the surface of the substrate (such as internal cells) are not considered to be "pores" for purposes of this invention. The pores have a number average diameter of from about 1 to 500 microns. Preferably, the number average diameter is from 10 to 300 microns and it is especially from 10 to 100 microns. A porous substrate may, for example, contain a pore volume of from 1 to 50, preferably from 5 to 20, $cm^3/g$; a surface area of from 10 to 500, preferably from 20 to 100 and more preferably from 25 to 75 $m^2/g$; and a density of from 8 to 400 $kg/m^3$, preferably from 24 to 108 $kg/m^3$. Any of the polymers described above can be used to form a porous substrate for use in this invention.

The dimensions and geometry of the substrate material are not considered to be critical and will be selected in each instance with the particular end-use application in mind. The substrate may be in the form of a sheet, a particulate, a tube, or any other convenient shape.

The surfaces of the substrate are substantially entirely coated with a ceramic coating that has a thickness of from 1 to 100 nanometers. The ceramic material can be any which (1) can be applied to the substrate at the mentioned coating thickness, (2) adheres to the substrate material and (3) is biocompatible. It is highly preferred that the ceramic material is one which can be applied in an atomic layer deposition process at a temperature low enough that the substrate does not decompose or become physically distorted (via melting or softening, for example) during the deposition process.

"Biocompatibility" can be determined for purposes of this invention according to the viability test that is described in the examples that follow. Viability of 50% or more of the cells under the conditions of this test is indicative of a biocompatible material.

Preferred ceramic coatings are aluminum oxide and titanium oxide coatings. "Aluminum oxide" is used herein to designate a coating that is made up substantially entirely of aluminum and oxygen atoms, without reference to the specific stoichiometry. In many cases, it is expected that an aluminum oxide coating will correspond somewhat closely to the empirical structure of alumina, i.e., $Al_2O_3$, although deviations from this structure are common and may be substantial. "Titanium oxide" is used herein to designate a coating that is made up substantially entirely of titanium and oxygen atoms, without reference to the specific stoichiometry. In most cases, it is expected that a titanium oxide coating will correspond closely to the empirical structure of titania, i.e., $TiO_2$, although deviations from this structure are common and may be substantial.

The ceramic coating preferably is from 1 to 50 nanometers thick and even more preferably from 1 to 20 nanometers thick. Ceramic coatings as thin as 1 to 10 nanometers have been found to be useful in this invention.

The ceramic coating is applied to the external surface of the substrate, and to the internal surfaces of any pores that are present in the substrate, and essentially completely covers those surfaces. The ceramic coating should cover at least 75%, preferably at least 90% and more preferably at least 95% and still more preferably at least 99% of the combined surface area of the exterior surfaces of the substrate and the interior surfaces of the pores.

The ceramic coating preferably is conformal. By "conformal", it is meant that the thickness of the coating layer is relatively uniform across the surfaces of the substrate (so that, for example, the thickest regions of the coating are no greater than 3× the thickness of the thinnest regions). When the ceramic coating is conformal, the surface shape of the coated substrate closely resembles that of the underlying substrate surface, and the general pore structure of the substrate is preserved. Pore diameters will to be slightly reduced due to the ceramic coating, but in most cases the coating thickness will be very small in relation to the pore diameter. The depth of individual pores may be reduced slightly for the same reason, and it is possible that very small pores may be completely filled.

Conformality is determined by methods such as transmission electron microscopy (TEM) that have resolution of 10 nm or below. Lower resolution techniques cannot distinguish conformal from non-conformal coatings at this scale. The surface is preferably coated by the ceramic layer substantially without pinholes or defects.

The ceramic coating is preferably deposited in an Atomic Layer Deposition (ALD) process. A suitable ALD process for depositing nanocoatings is described in U.S. Pat. Nos. 6,613,383, 6,713,177, U.S. Published Patent Application No. 2004/0224087 and WO 03/008186A1. In the ALD process, the coating-forming reaction is conducted as a series of (typically) two half-reactions. In each of these half-reactions, a single reagent is introduced into contact with the substrate surface. Conditions are such that the reagent is in the form of a gas. The reagent deposits on the surface of the substrate. In most cases it reacts with functional groups on the surface of the substrate and becomes bound to the substrate. Because the reagent is a gas, it permeates into pores in the substrate and deposits onto the interior surfaces of the pores as well as onto the exterior surfaces of the substrate. Excess amounts of the reagent are then removed, which helps to prevent the growth of undesired, larger inclusions of the coating material. Each remaining half-reaction is then conducted in turn, each time introducing a single reagent, allowing it to react at the surface of the particle, and removing excess reactant before introducing the next reagent. Usually, a carrier gas is used to introduce the reagents, and the reaction chamber usually is swept with the carrier gas between successive reagent introductions to help remove excess reagents and gaseous reaction products. A vacuum may be pulled between successive dosings of reagents, in order to further remove excess reagents and gaseous reaction products.

Atomic layer controlled growth techniques permit the deposition of coatings of about 0.1 to 5 angstroms in thickness per reaction cycle, and thus provide a means of extremely fine control over coating thickness. Thicker coatings can be prepared by repeating the reaction sequence to sequentially deposit additional layers of the coating material until the desired coating thickness is achieved.

A convenient method for applying the coating to a particulate substrate is to form a fluidized bed of the particles, and then pass the various reagents in turn through the fluidized bed under reaction conditions. Methods of fluidizing particulate materials are well known, and generally include supporting the particles on a porous plate or screen. A fluidizing gas is passed upwardly through the plate or screen, lifting the particles somewhat and expanding the volume of the bed. With appropriate expansion, the particles behave much as a fluid. Fluid (gaseous or liquid) reagents can be introduced into the bed for reaction with the surface of the particles. In this invention, the fluidizing gas also can act as an inert purge gas for removing unreacted reagents and volatile or gaseous reaction products.

In addition, the reactions can be conducted at particle surfaces in a rotating cylindrical vessel or a rotating tube. This method is particularly suitable for continuous processes.

Reaction conditions are selected mainly to meet three criteria. The first criterion is that the reagents are gaseous under the conditions of the reaction. Therefore, temperature and pressure conditions are selected such that the reactants are volatilized. The second criterion is one of reactivity. Conditions, particularly temperature, are selected such that the desired reaction between the film-forming reagents (or, at the start of the reaction, the first-introduced reagent and the particle surface) occurs at a commercially reasonable rate. The third criterion is that the substrate is thermally stable, from a chemical standpoint and from a physical standpoint. The substrate should not degrade or react at the process temperature, other than a possible reaction on surface functional groups with one of the ALD precursors at the early stages of the process. Similarly, the substrate should not melt or soften at the process temperature, so that the physical geometry, especially pore structure, of the substrate is maintained. The reactions are generally performed at temperatures from about 270 to 1000 K, preferably from 290 to 450 K, with specific temperatures in each case being below the temperature at which the substrate melts, softens or degrades.

Between successive dosings of the reagents, the particles are subjected to conditions sufficient to remove reaction products and unreacted reagents. This can be done, for example, by subjecting the particles to a high vacuum, such as about $10^{-5}$ Torr or greater, after each reaction step. Another method of accomplishing this, which is more readily applicable for industrial application, is to sweep the particles with an inert purge gas between the reaction steps. This purge gas can also act as a fluidizing medium for the particles and as a carrier for the reagents.

Several techniques are useful for monitoring the progress of the reaction. For example, vibrational spectroscopic studies can be performed using transmission Fourier transform infrared techniques. The deposited coatings can be examined using in situ spectroscopic ellipsometry. Atomic force microscopy studies can be used to characterize the roughness of the coating relative to that of the surface of the substrate. X-ray photoelectron spectroscopy and x-ray diffraction can be used to do depth-profiling and ascertain the crystallographic structure of the coating.

Aluminum oxide coatings are conveniently deposited using trimethylaluminum and water as the precursors, as illustrated by reaction sequence A1/B1. The illustrated reactions are not balanced, and are only intended to show the reactions at the surface of the substrate (i.e., not inter- or intralayer reactions).

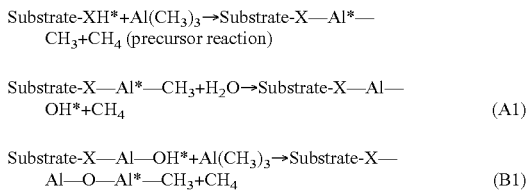

Substrate-XH*+Al(CH$_3$)$_3$→Substrate-X—Al*—CH$_3$+CH$_4$ (precursor reaction)

Substrate-X—Al*—CH$_3$+H$_2$O→Substrate-X—Al—OH*+CH$_4$     (A1)

Substrate-X—Al—OH*+Al(CH$_3$)$_3$→Substrate-X—Al—O—Al*—CH$_3$+CH$_4$     (B1)

In reactions A1/B1, X is typically oxygen, nitrogen or sulfur, and the asterisk (*) represents the surface species at which the next half-reaction can occur. An aluminum oxide film is built up by repeating reactions A1 and B1 in alternating fashion, until the desired coating thickness is achieved. Aluminum oxide films tend to grow at a rate of approximately 0.3 nm/cycle using this reaction sequence.

Titanium oxide coatings are conveniently deposited using titanium tetrachloride and water and/or hydrogen peroxide as the precursors, as illustrated by reaction sequence A2/B2. As before, the illustrated reactions are not balanced, and are only intended to show the reactions at the surface of the particles (i.e., not inter- or intralayer reactions).

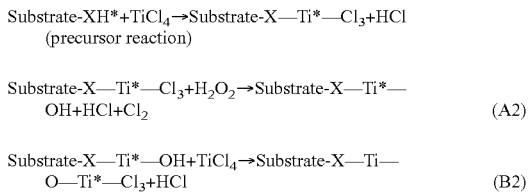

Substrate-XH*+TiCl$_4$→Substrate-X—Ti*—Cl$_3$+HCl (precursor reaction)

Substrate-X—Ti*—Cl$_3$+H$_2$O$_2$→Substrate-X—Ti*—OH+HCl+Cl$_2$     (A2)

Substrate-X—Ti*—OH+TiCl$_4$→Substrate-X—Ti—O—Ti*—Cl$_3$+HCl     (B2)

In reactions A2/B2, X is typically oxygen, nitrogen or sulfur, and the asterisk (*) represents the surface species at which the next half-reaction can occur. A titanium oxide film is built up by repeating reactions A2 and B2 in alternating fashion, until the desired coating thickness is achieved. Titanium oxide films tend to grow at a rate of approximately 0.05-0.1 nm/cycle using this reaction sequence.

The coated substrate can be used as all or a portion of a wide variety of implanted devices. These include, for example, devices such as stents, catheters, synthetic blood vessels, artificial joints, bone rods, screws, implanted dental devices, pacemaker or defibrillator housings or leads, as various types of implanted protheses, and the like.

The coated substrate of the invention is particularly useful as a tissue engineering scaffold. The tissue engineering scaffold is useful for making artificial tissues of various types.

Artificial tissues are produced according to the invention by attaching living cells to the coated substrate, which serves as the tissue engineering scaffold. As mentioned, the tissue engineering scaffold is preferably porous, and the interior surfaces of the pores are preferably substantially entirely coated with the ceramic coating as described before. Living cells can be attached to the tissue engineering scaffold in any convenient manner, including those methods described in U.S. Pat. No. 7,338,517. Generally, a suspension of the cells in a culture medium is placed in contact with the tissue engineering scaffold, and the cells are then cultured in vitro in the presence of the scaffold. The cell suspension generally is a medium which promotes growth of the cells. Culturing conditions will of course depend on the particular cells, but for mammalian cells the temperature of the medium should closely approximate the normal body temperature of the particular mammal that supplied the cells. For humans, this temperature is about 37° C.

The cells may attach to the exterior surfaces of the tissue engineering scaffold, in the pores of the tissue engineering scaffold, or both.

The cells can be from any living organism, but preferably are mammalian cells and more preferably are human cells. In especially preferred embodiments, the cells are taken from the specific individual in which the artificial tissue will be implanted. This tends to minimize tissue rejection and similar complications.

The living cells may be, for example, myocyte precursor cells, cardiac myocytes, skeletal myocytes, satellite cells, fibroblasts, cardiac fibroblasts, chondrocytes, osteoblasts, endothelial cells, epithelial cells, embryonic stem cells, hematopoietic stem cells, neuronal cells, mesenchymal stem cells, anchorage-dependent cell precursors, or combinations thereof. Two or more different types of cells can be attached to the tissue engineering scaffold.

The resulting artificial tissue can be implanted into an animal body to repair or replace diseased, injured, damaged or malformed tissues. The animal is typically mammalian and preferably human. Typically, the artificial tissue is implanted surgically, but the artificial tissue in some instances can be implanted by injection, and in other cases, such as artificial epidermal tissue, the artificial tissue can be implanted by being contacted with an open wound. No special techniques are necessary to implant the artificial tissue of the invention. Among the types of treatment that can be performed using the artificial tissue are replacement of vessels such as coronary arteries; physiologic tubular structures such as ureters, veins, lymph channels, GI tract components and the like; repair of injured or diseased bone; repair of damaged nervous tissues, repair or replacement of connective tissues such as ligaments and tendons, correction of impaired cardiac function, repair or replacement of damaged or diseased skin tissue; repair of muscle tissue; hernia repairs, repair of endocrine tissues and/or lymphatic tissues, repair or replacement of cartilage, and the like.

The artificial tissue can be engineered to contain and release pharmacologic agents such as cytokines. These agents may affect cell proliferation, development, migration, differentiation or activity, as appropriate for the specific application. Pharmacologic agents of these types include, for example, epidermal growth factor, vascular endothelial growth factor, fibroblast growth factor, erythropoietin, hematopoietic cell growth factor, platelet-derived growth factor, stem cell factors, bone morphogenic protein, fibronectin, transforming growth factors alpha and beta, nerve growth factor, and neurotrophins.

The ceramic-coated substrates of the invention exhibit good adhesion to apatite, which suggests that these materials will be very useful in replacing or repairing bone structures. Similarly, proteins tend to adhere well to the ceramic-coated substrates, which suggests that they will exhibit good adhesion to cellular material in vivo.

If the substrate is biodegradable, such that it can be broken down in the body to form innocuous products, it is possible that the ceramic-coated substrate will be similarly biodegradable, except for the ceramic coating. Because the ceramic coating is extremely thin, it may be susceptible to cracking or the formation of other defects in the body, which allow the underlying substrate to be exposed to body fluids and be biodegraded. In such as case, the substrate will biodegrade normally, although the rate at which it biodegrades may be significantly lower than that of the uncoated material. The ceramic coating may tend to remain attached to the oligomeric materials that form as the polymer becomes biodegraded. In that case, the ceramic portion of the material can be excreted from the body through normal biological pathways. The ceramic coating may instead remain in the body after the substrate has degraded. This is not considered to represent a problem, because the ceramic coating is generally biocompatible, and because the amount of ceramic material is very small due to the extremely thin films that are present.

The following examples are provided to illustrate coating processes applicable to making the particles of the invention. These examples are not intended to limit the scope of the inventions. All parts and percentages are by weight unless otherwise indicated.

EXAMPLE 1

Macroporous poly(styrene-divinylbenzene) (PS-DVB) particles (~85% porosity, 8-10 cm$^3$/g pore volume, 43.5 m$^2$/g surface area, 70 kg/M$^3$ particle density and ~600 μm diameter) are coated with different thickness of aluminum oxide films by alternating exposure of deionized water and trimethylaluminum (TMA) in a vibrating fluidized bed reactor. The fluidized bed is 3.5 cm in diameter. There is a metal disc with 10 μm pores in the middle of the reactor which serves as the dosing header. The reactor is encased by a clamshell-type furnace and bolted to a platform that rests on four large springs. The reactor is maintained at low pressure using a vacuum pump, and the dosing header can also be pumped down directly using a smaller separate pump. A vibration system is used to overcome some of the interparticle attractive forces and improve the quality of fluidization. High purity nitrogen gas is used as the purge gas to remove unreacted precursor and any by-products formed during the reaction. The nitrogen flow rate is controlled by a mass flow controller. Piezoelectric transducers are located below the distributor plate and at the outlet of the reactor column to measure the pressure drop across the bed of the particles. All valves used to provide the transient dosing are computer controlled. A mass spectrometer is connected to the reactor to track the reaction so that the dose time of precursors can be optimized.

~4 g of the macroporous polymer particles are loaded into the reactor. The pressure inside the reactor is reduced to ~50 mtorr, and the particles are outgassed for 24 hours. The temperature inside the reactor is adjusted to 33° C. and maintained at that temperature throughout the ALD reaction sequence. Nitrogen gas is fed in to provide a minimum fluidization superficial gas velocity of 0.8 cm/s determined by measuring the pressure drop across the bed versus the $N_2$ superficial gas velocity. Trimethylaluminum (TMA) and deionized $H_2O$ are fed separately in alternating fashion through the distributor of the reactor using the driving force of their vapor pressures. The flow rates of TMA and $H_2O$ are adjusted using needle valves to ensure that a precursor pressure (~3 torr) is high enough in each case to fluidize the particles. The dosing sequence for each cycle is TMA dose, nitrogen purge, evacuation to 50 mtorr, water dose, nitrogen purge, evacuation to 50 mtorr. TMA and water dose times are each 60 seconds. 25 reaction cycles are performed.

TEM samples are prepared by crushing the coated macroporous particles and placing micron-sized pieces on holey-carbon films supported on Cu grids. Z-contrast imaging of the coated samples is performed using a JEOL 2010F 200 kV Schottky field emission transmission electron microscope operating in the scanning transmission electron microscopy (STEM) mode with an electron probe size of 0.2 nm.

The aluminum oxide films appear very uniform and smooth. The thickness of the aluminum oxide films is ~7 nm, which represents a growth rate of ~0.3 nm per coating cycle at this experimental condition.

Samples are prepared for cross-sectional TEM by cutting epoxy resin cured porous polymer at the temperature of −100° C. using a diamond knife. The cross sectional TEM image of the aluminum oxide-coated macroporous polymer particles is shown in FIG. 1. The black "threads" that appear in FIG. 1 are aluminum oxide films on the surface of the polymer pores. The aluminum oxide films appear very uniform and smooth. There are no aluminum oxide films on the walls of some pores. In these cases, the aluminum oxide films are believed to have been peeled off during the cutting process.

The deposition of aluminum oxide films inside the pore structure is further confirmed by FESEM and EDS measurements. FESEM specimens are prepared by cutting the coated particles using a Super Gillette blue blade. The EDS mapping signal illustrates the presence of aluminum oxide throughout the inner surface of the porous particles, which confirms the presence of aluminum oxide films are distributed homogeneously on the polymer surface and on the inside of the pores.

EXAMPLE 2

Titanium oxide films are deposited on macroporous polymer particles in the same general manner as described in Example 1. The ALD precursors in this case are $TiCl_4$ and a 50% by weight solution of $H_2O_2$ in $H_2O$. The reaction temperature is 100° C., which is still much lower than the softening/melting point of the porous polymer particles. Before the reaction, the particles are outgassed at 100° C. for 24 hours. 50 reaction cycles are performed. Z-contrast imaging of the titanium oxide coated polymer particles show that the titanium oxide films are very uniform and smooth, and have a thickness of 3 nm, which represents a growth rate of 0.06 nm per coating cycle at this experimental condition. Titanium oxide films are conformally grown on internal and external polymer particle surfaces.

Viability Testing of the Coated Porous Polymer Particles from Examples 1 and 2

Uncoated macroporous polymer particles and coated particles from Example 1 and 2 are separately extracted for one week in cell growth media (30 mg particles/mL media) (Dulbecco's Modified Eagle's Medium (Invitrogen) supplemented with 10% fetal bovine serum (FBS, Invitrogen)). The growth media is then removed from the particles and various dilutions are prepared. The dilutions correspond to extractions using particle concentrations of 30 (undiluted), 10, 5, 1, 0.5 and 0.1 mg/mL.

NIH/3T3 (ATCC) fibroblast cells are plated at $10^4$ cells/well and cultured in the wells of a 96 well tissue culture treated plate. Cells are allowed to attach for 1 day. Thereafter, the culture medium in each well is replaced with the extract from the uncoated polymer particles or that from Example 1 or Example 2, at the various dilutions specified above. Cells are then cultured for 3 days in the presence of the extractant. Controls are cultured in normal cell growth media. Cell viability is determined by the 3-(4,5-Dimethyl-2-thiazolyl)-2,5-diphenyl-2H-tetrazolium bromide (MTT) colorimetric assay method, which depends on the ability of viable cells to metabolize a water-soluble yellow dye to a water-insoluble purple dye. At all dilution levels tested, cell viability in the extracts from Example 1 and Example 2 coated particles is similar to cell viability in the extract from the uncoated polymer particles. Cell viability is ~50-60% when the cell is cultured in extracts from the aluminum oxide- and titanium oxide-coated samples that correspond to concentrations from 0.1 to 10 mg/mL of the particles in the medium.

Apatite Formation on Aluminum Oxide and Titanium Oxide Coated Porous Polymer Particles In vitro bioactivity studies of the composite are assessed by immersion in a simulated body fluid (SBF) for different periods of time. Coated particles obtained in Examples 1 and 2 are separately incubated in a simulated body fluid (SBF) that is prepared by dissolving NaCl, NaHCO$_3$, KCl, K$_2$HPO$_4$.3H$_2$O, MgCl$_2$.6H$_2$O, CaCl$_2$, and Na$_2$SO$_4$ in deionized water and buffering at a pH value of 7.3 at 37° C. with tri-(hydroxymethyl)aminomethane [(CH$_2$OH)$_3$CNH$_2$] and hydrochloric acid (HCl). The resulting ion concentrations are nearly equal to those of human blood plasma. The SBF solution is changed every 2~3 days. After incubation at 37° C. for one or two weeks, polymer particles are removed from SBF, rinsed gently with deionized water twice, and vacuum dried overnight.

Figure 2A:
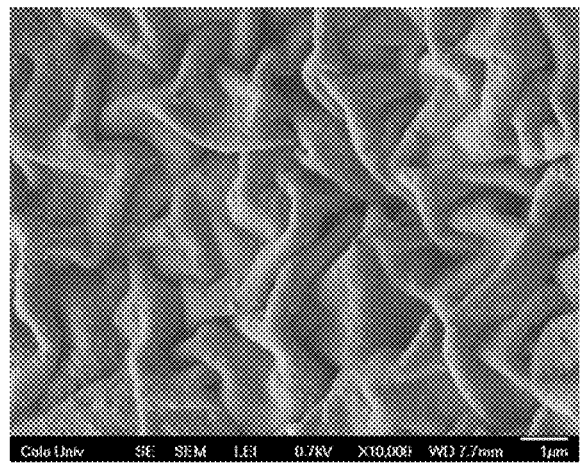
FIG. 2a is an FESEM micrograph of a porous styrene-divinylbenzene copolymer having an atomic layer deposition aluminum oxide layer, prior to incubation in simulated body fluid.
Figure 2B:
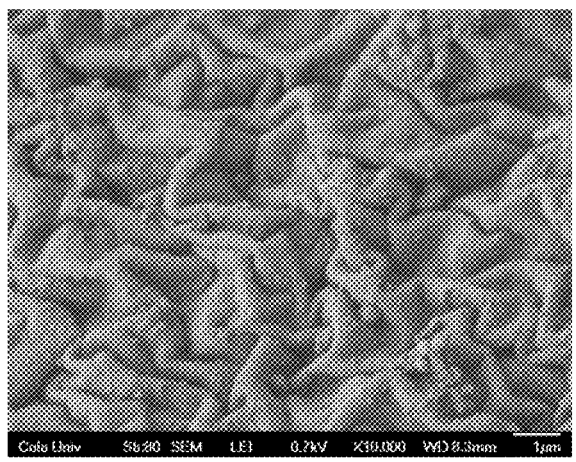
FIG. 2b is an FESEM micrograph of the same porous styrene-divinylbenzene copolymer having an atomic layer deposition aluminum oxide layer as shown in FIG. 2a, after one week of incubation in simulated body fluid.
Figure 2C:
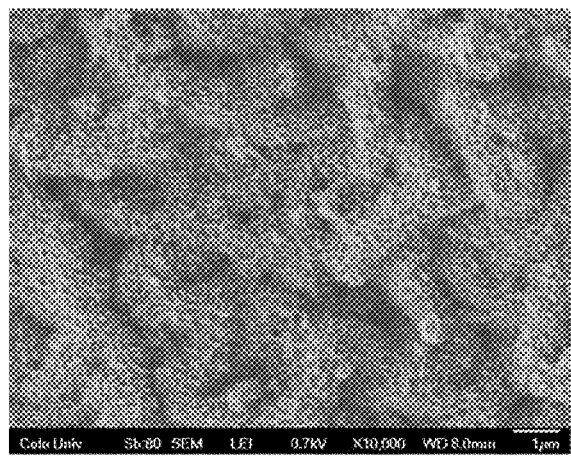
FIG. 2c is an FESEM micrograph of the same porous styrene-divinylbenzene copolymer having an atomic layer deposition aluminum oxide layer as shown in FIG. 2a, after two weeks of incubation in simulated body fluid.

FESEM examination of the resulting samples show changes in the appearance and microstructure of the materials after 1 and 2 weeks of incubation in SBF. FIGS. 2a, 2b and 2c, respectively, are FESEM images of Example 1 particles before incubation, after incubation for one week, and after incubation for two weeks. As shown in FIG. 2b, after one week, the surface of the particle becomes rough and some small particles are formed on the surface. This indicates the formation of stoichiometric or non-stoichiometric bone-like apatite. After 2 weeks, the amount of bone-like apatite greatly increases, as shown in FIG. 2c. At that point, nanoscale bone-like apatite particles are homogeneously dispersed on the particle surface and the formed particles seem to be well-bonded to the substrate surface, as shown in FIG. 2c. The particle surface appears considerably rougher compared to the particle surface before apatite formation. Energy dispersive spectrometry (EDS) is performed to analyze the composition of the films formed on the composite surface of the sample that has been incubated for two weeks. The EDS spectrum shows that a considerable amount of calcium and phosphorus is present, typical of bone-like apatite.

Figure 3A:
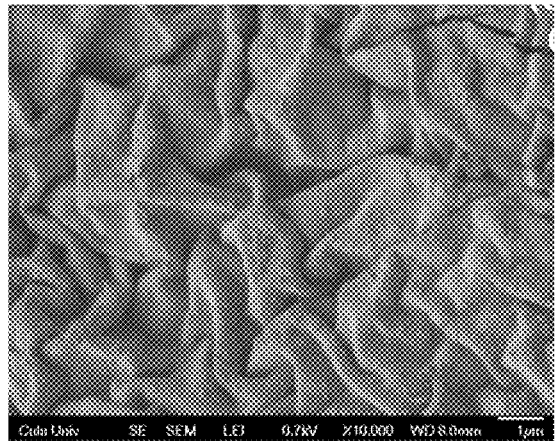
FIG. 3a is an FESEM micrograph of a porous styrene-divinylbenzene copolymer having an atomic layer deposition titanium oxide layer, prior to incubation in simulated body fluid.
Figure 3B:
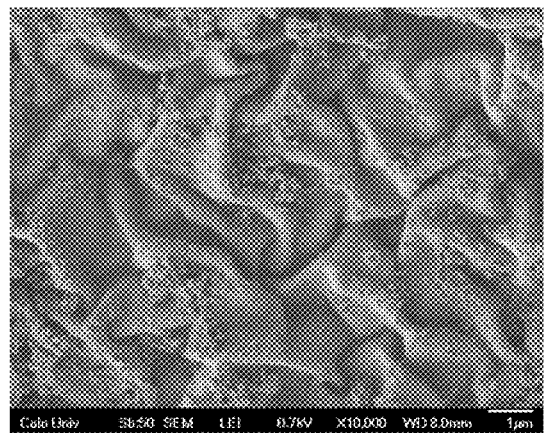
FIG. 3b is an FESEM micrograph of the same porous styrene-divinylbenzene copolymer having an atomic layer deposition titanium oxide layer as shown in FIG. 3a, after one week of incubation in simulated body fluid.
Figure 3C:
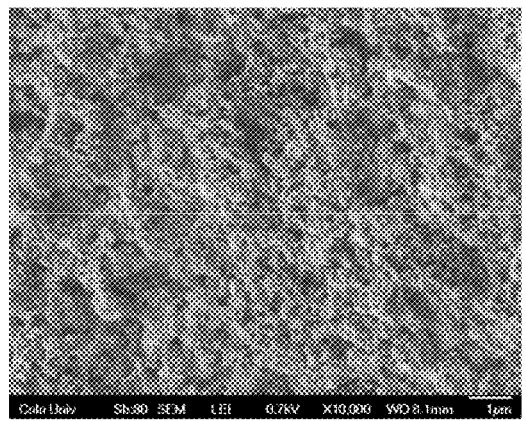
FIG. 3c is an FESEM micrograph of the same porous styrene-divinylbenzene copolymer having an atomic layer deposition titanium oxide layer as shown in FIG. 3a, after two weeks of incubation in simulated body fluid.

FIGS. 3a, 3b and 3c are FESEM images of coated Example 2 particles after zero, one week, and two weeks, respectively, incubation in SBF. As shown in FIG. 3b, after one week, the surface of the particle becomes rough and some small particles are formed, which clearly indicates the formation of stoichiometric or non-stoichiometric bone-like apatite. After 2 weeks, the amount of bone-like apatite greatly increases, and nanoscale bone-like apatite particles are homogeneously dispersed on the particle surface. The formed particles seem to be well-bonded to the substrate surface, as shown in FIG. 3c. An EDS spectrum of the films again confirms that a considerable amount of calcium and phosphorus is present in the films.

The grain size of apatite formed on Example 2 particles is much larger than the size of those formed on the Example 1 particles, which indicates that the titanium oxide surface more greatly favors the growth of apatite and that the growth rate of apatite on titanium oxide films is much faster than on aluminum oxide films.

By contrast, apatite formation on the uncoated starting polymer particles under the same conditions is very slow. After two weeks of incubation in SBF, there is no homogeneous distribution of bone-like apatite and EDS analysis indicates only trace amounts of calcium and phosphorus are present in the films.

To ensure that apatite has been formed within the pores of the Example 1 and Example 2 particles, FESEM specimens are prepared by cutting the coated particles using a Super Gillette blue blade. Phosphorus and calcium EDS indicates the presence of apatite throughout the inner surface of the coated particles, confirming that apatite is formed inside the pores as well as on the polymer surface.

Protein Adsorption on Aluminum Oxide and Titanium Oxide Coated Particles

The protein adsorption of the Example 1 and Example 2 particles, as well as the uncoated starting polymer particles, is evaluated using fetal bovine serum (FBS). The aluminum oxide and titanium oxide coated PS-DVB particles are separately incubated in FBS at 37° C. for 24 hours. The particles are then removed, rinsed gently with distilled water twice, and freeze dried. The amount of protein adsorbed on the particles is estimated by analyzing the nitrogen signal using a PHI 5600 physical electronics X-ray photoelectron spectroscope (XPS) with a high-energy resolution analyzer.

The Example 1 and Example 2 particles each show a significantly greater nitrogen signal than the uncoated particles, indicating a significantly greater protein absorption. The titanium oxide-coated particles of Example 2 show much more protein absorption by this test than do the aluminum oxide-coated particles of Example 1. These results indicate that the aluminum oxide and titanium oxide-coated polymer particles may have better cell adhesion, which is important for bone tissue engineering applications.

What is claimed is:

1. An artificial tissue comprising living cells attached to a porous tissue engineering scaffold comprising a porous polymer having a conformal aluminum oxide coating, a titanium oxide coating, or both an aluminum oxide and a titanium oxide coating adherent to the surface of the porous polymer, wherein the porous polymer is a nonabsorbable polymer selected from a polyethylene polymer, a polyethylene copolymers, a styrene homopolymer, a styrene copolymer, a polyurethane, a polypropylene homopolymer, a propylene copolymer, a polyamide, a polyalkyleneterephthalate, a polyvinylidene fluoride, a polycarbonate, a polymer of an acrylate ester, a polymer of a methacrylate ester, a polyether, and polytetrafluoroethylene, and wherein the coating has a thickness of from about 1 to 20 nanometers and covers at least 95% of the external surface of the porous polymer and internal surfaces of the pores.

2. A method for producing an artificial tissue, comprising (a) forming a tissue engineering scaffold by applying a conformal aluminum oxide coating, a titanium oxide coating, or both an aluminum oxide and a titanium oxide coating to the external surface and the internal surfaces of the pores of a porous polymer via an atomic layer deposition process such that the coating has a thickness of from 1 to 20 nanometers and covers at least 95% of the external surface of the porous polymer and internal surfaces of the pores and (b) growing cells in the presence of the tissue engineering scaffold such that living cells become attached to the tissue engineering scaffold, wherein the porous polymer is a nonabsorbable polymer selected from a polyethylene polymer, a polyethylene copolymers, a styrene homopolymer, a styrene copolymer, a polyurethane, a polypropylene homopolymer, a propylene copolymer, a polyamide, a polyalkyleneterephthalate, a polyvinylidene fluoride, a polycarbonate, a polymer of an acrylate ester, a polymer of a methacrylate ester, a polyether, and polytetrafluoroethylene.

3. A method for repairing or replacing tissue in a mammal, comprising implanting an artificial tissue of claim 1 to a living mammal.

4. A method for repairing or replacing tissue in a mammal, comprising implanting an artificial tissue produced in accordance with claim 2 to a living mammal.

5. The process of claim 2, wherein in the atomic layer deposition process, the coating is applied in a series of two half-reactions in which, in each half-reaction, a single gaseous reagent is introduced into contact with the substrate surface and permeated into pores into the substrate and deposits onto interior surfaces of the pores and onto exterior surfaces of the substrate, and excess amounts of the reagent are removed prior to performing the next half-reaction.

6. The process of claim 5 wherein the reagents for the half-reactions are trimethylaluminum and water, and the coating is aluminum oxide.

7. The process of claim 5 wherein the reagents for the half-reactions are titanium tetrachloride and water or hydrogen peroxide, and the coating is titanium oxide.

8. An artificial tissue comprising living cells attached to a porous tissue engineering scaffold produced in the process of claim 2.

9. An artificial tissue comprising living cells attached to a porous tissue engineering scaffold produced in the process of claim 5.

10. An artificial tissue comprising living cells attached to a porous tissue engineering scaffold produced in the process of claim 6.

11. An artificial tissue comprising living cells attached to a porous tissue engineering scaffold produced in the process of claim 7.

* * * * *